United States Patent [19]

Kastrubin et al.

[11] 4,140,133

[45] Feb. 20, 1979

[54] DEVICE FOR PULSE CURRENT ACTION ON CENTRAL NERVOUS SYSTEM

[75] Inventors: Eduard M. Kastrubin; Valentin M. Nozhnikov, both of Moscow, U.S.S.R.

[73] Assignee: Moskovsky Oblastnoi Nauchno-Issledovatelsky Institut Akusherstva I Ginekolog II, U.S.S.R.

[21] Appl. No.: 791,151

[22] Filed: Apr. 26, 1977

[51] Int. Cl.² .............................................. A61N 1/36
[52] U.S. Cl. .................................. 128/421; 128/1 C
[58] Field of Search ........................ 128/1 C, 421, 422

[56] References Cited

U.S. PATENT DOCUMENTS

| | | | |
|---|---|---|---|
| 1,908,688 | 5/1933 | Call | 128/421 |
| 2,993,178 | 7/1961 | Burger | 128/421 |
| 3,989,051 | 11/1976 | Nozhnikov et al. | 128/421 |

FOREIGN PATENT DOCUMENTS 148150  1/1962  U.S.S.R. ................................. 128/1 C

*Primary Examiner*—William E. Kamm
*Attorney, Agent, or Firm*—Steinberg & Blake

[57] ABSTRACT

A device for pulse current action on the central nervous system includes a current pulse preamplification unit and a unit for adjusting a value of an additional constant component. The current pulse preamplification unit is coupled via a switch to the current pulse duration adjusting unit of the device to produce the second level of the first stage of general electroanesthesia, or to the intermittent analgesia unit of the device to make it possible to anesthetize growing pain. The unit for adjusting the additional constant component value is connected to the power unit of the device. This permits the reduction of the impedance at the points where the electrodes are attached to the forehead and neck areas. The current pulse preamplification unit and the unit for adjusting the additional constant component value are connected to the power unit and the patient protection unit of the device to limit the general electroanesthesia level in accordance with a prescribed anesthesia and treatment program, while performing current pulse action of the patient's central nervous system. The outputs of the current pulse preamplification unit and the unit for adjusting the additional constant component value are connected to the inputs of the current pulse amplitude adjusting unit of the device, which, in turn, is connected to the current pulse amplitude indicator of the device.

4 Claims, 2 Drawing Figures

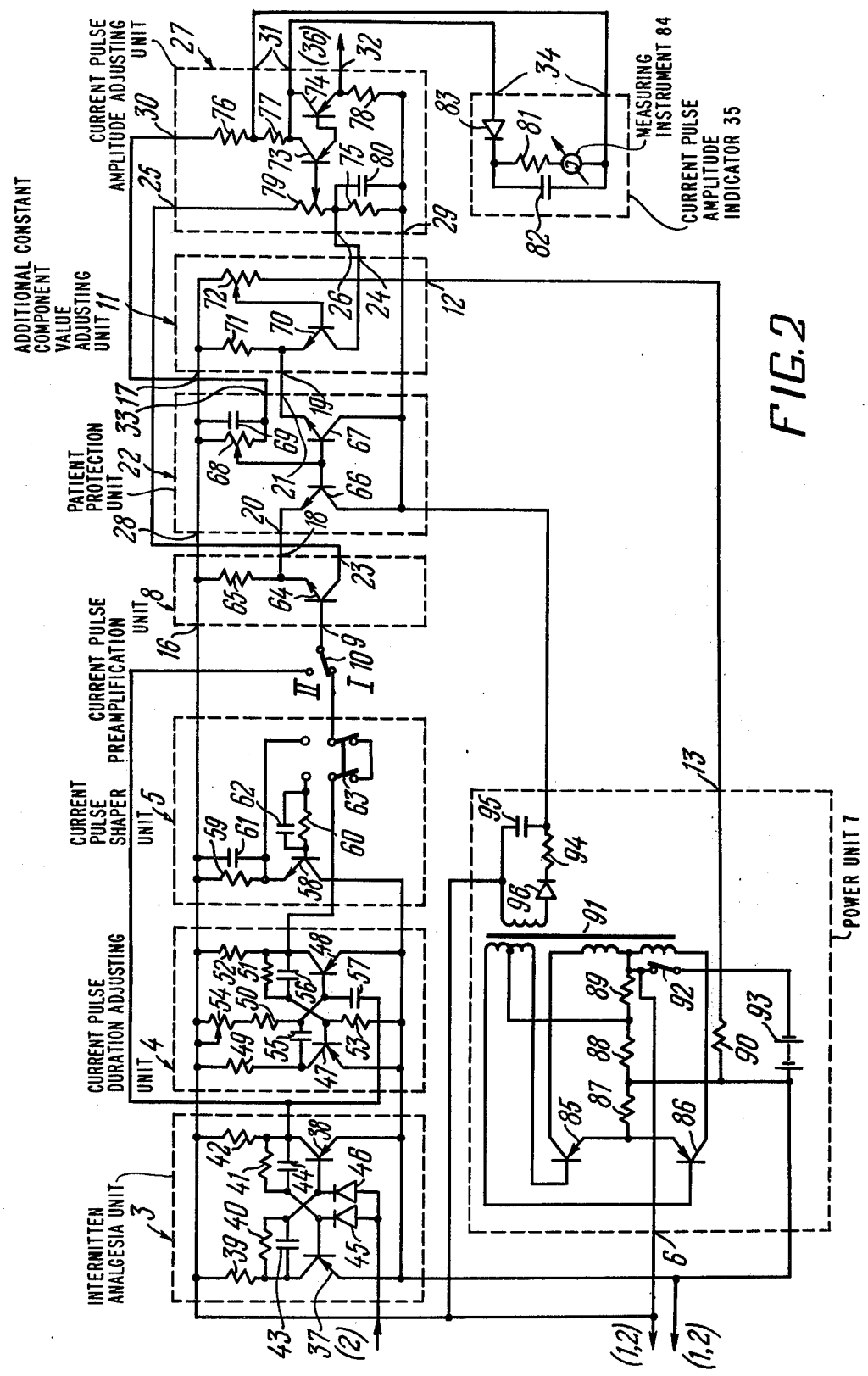

DEVICE FOR PULSE CURRENT ACTION ON CENTRAL NERVOUS SYSTEM

BACKGROUND OF THE INVENTION:

The present invention relates to an improvement in a device for pulse current action on the central nervous system.

The invention is applicable for carrying out a prescribed anesthesia and treatment program, for example, in the course of child delivery.

There is known a device for pulse current action on the central nervous system (U.S. Pat. No. 3,989,051), wherein current pulses are applied to a patient through electrodes, i.e., a cathode attached in the forehead area and an anode attached in the neck area, under the mastoids, in order to produce the second level of the first stage of general electroanesthesia in the central nervous system of the patient. Current pulses are supplied from a unit for rhythmic action by current pulses on the central nervous system, a unit for adjusting the duration of current pulses or an intermittent analgesia unit, a switch, a unit for adjusting the amplitude of current pulses and a mean current intensity indicator, which makes it possible to produce the second level of the first stage of general electroanesthesia without any side effects on the patient. The units are connected in series. The application of current pulses is discontinued by a patient protection unit if the amplitude of current pulses is in excess of a preselected value.

In this device, the output of the patient protection unit is so connected to the input of the power unit that said patient protection unit disconnects the power unit from the unit for rhythmic current pulse action on the central nervous system, the unit for adjusting the duration of current pulses, the intermittent analgesia unit and the unit for adjusting the amplitude of current pulses, if the amplitude of current pulses is above a preselected value.

In order to mitigate pain in the course of electroanesthesia, the operation of the device must be discontinued by disconnecting the power unit from the above-mentioned units, which discontinues the current pulse action on the central nervous system, sharply reduces the effects of electroanesthesia, and prevents the use of the second level of the first stage of general electroanesthesia necessary for anesthesia and treatment.

It has been established that while performing anesthesia and treatment with current pulses, it is necessary to stabilize the second level of the first stage of general electroanesthesia once it has been achieved, without any further increase in the mean current intensity in the patient circuit even in case of a change in the impedance at the points where the electrodes are attached, which may be caused by a change in the functional state of the central nervous system.

It is an object of the present invention to improve the device for pulse current action on the central nervous system to ensure a desired pulse action level for each patient in accordance with a prescribed anesthesia and treatment program.

It is another object of the invention to improve the device for pulse current action on the central nervous system to permit the limitation of the mean current intensity in the patient circuit without discontinuing operation of the device in case of a reduction in the impedance in the electrode areas, caused by a change in the functional state of the patient's central nervous system.

The foregoing objects are attained by providing a device for pulse current action on the central nervous system, wherein current pulses are applied to a patient through electrodes, i.e., a cathode attached in the forehead area and an anode attached in the neck area, under the mastoids, in order to produce the second level of the first stage of general electroanesthesia in the central nervous system of the patient. In the device of the invention, current pulses are applied to the patient from a number of series connected units which include a unit for rhythmic current pulse action on the central nervous system, an intermittent analgesia unit or a unit for adjusting the duration of current pulses, a switch, a unit for adjusting the amplitude of current pulses and a mean current intensity indicator, which makes it possible to produce the second level of the first stage of general electroanesthesia without any side effects on the patient. The second level of the first stage of general electroanesthesia is stabilized by a patient protection unit. The device of the invention further includes a current pulse preamplification unit whose input is electrically coupled via the switch to the output of the unit for adjusting the duration of current pulses so as to produce the second level of the first stage of general electroanesthesia, or to the output of the intermittent analgesia unit so as to counteract growing pain, and a unit for adjusting the value of an additional constant component, whose input is connected to the output of a power unit, which makes it possible to reduce the impedance at the points where the electrodes are attached in the forehead and neck areas. Other inputs of the current pulse preamplification unit and the unit for adjusting the value of the additional constant component are connected to the power unit and the outputs of the patient protection unit so as, while acting with current pulses on the central nervous system, to limit the level of general elctroanesthesia in accordance with an anesthesia and treatment program prescribed for each patient. The outputs of the units are connected to the inputs of the unit for adjusting the amplitude of current pulses. The patient protection unit is connected to the power unit. The input of a current pulse amplitude indicator is connected to one of the outputs of the unit for adjusting the amplitude of current pulses.

The proposed device for pulse current action on the central nervous system makes it possible to perform current pulse anesthesia and treatment during prolonged periods of time, and ensures complete electric safety of the patient and a stable level of general electroanesthesia. The invention makes it unnecessary for a physician to attend to a patient throughout a period of application of electroanesthesia or to control the intensity of current pulse action on the central nervous system of the patient.

BRIEF DESCRIPTION OF THE DRAWINGS:

Other objects and advantages of the present invention will be more fully understood from the following detailed description of a preferred embodiment thereof to be read in conjunction with the accompanying drawings, wherein:

FIG. 2 is a circuit diagram of the device of FIG. 1 without the unit for rhythmic current pulse action on the central nervous system, the unit for separate adjustment of the repetition frequency and duration of current pulses, and the mean current intensity indicator.

Figure 1:
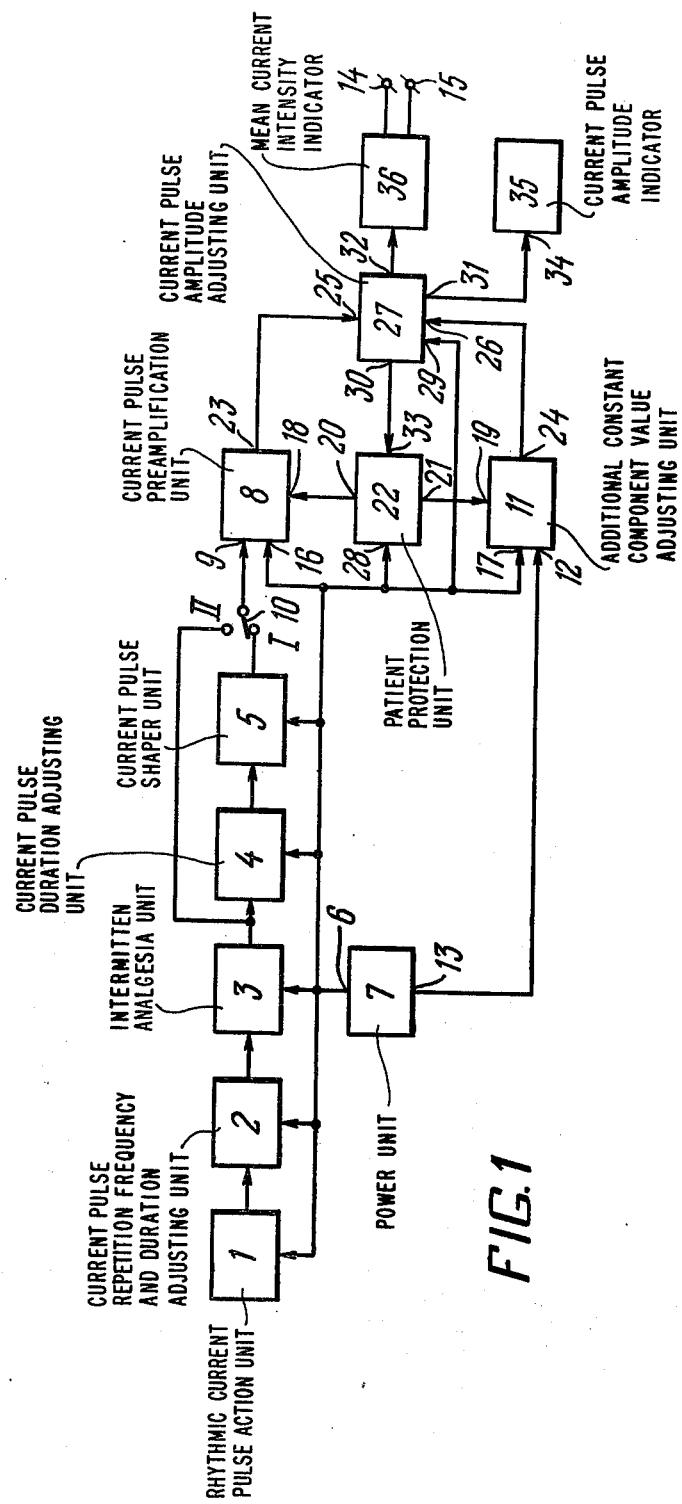
FIG. 1 is a block diagram of the device of the invention for pulse current action on the central nervous system.

DETAILED DESCRIPTION OF THE INVENTION:

Referring to the attached drawings, the proposed device for pulse current action on the central nervous system comprises the series connection of a unit 1 (FIG. 1) for rhythmic current pulse action on the central nervous system and a unit 2 for separate adjustment of the repetition frequency and duration of current pulses, intended to ensure a specific approach to each patient after producing the second level of the first stage of general electroanesthesia in the patient's central nervous system. The device further includes an intermittent analgesia unit 3 to ensure analgesia from contraction to contraction in the course of child delivery. A unit 4 adjusts the duration of current pulses, intended to produce the second level of the first stage of general electroanesthesia without any side effects on the patient. A unit 5 changes the shape of current pulses, intended to produce the second level of the first stage of general electroanesthesia in weak patients and children. The foregoing units are connected to an output 6 of a power unit 7.

The device still further includes a current pulse preamplification unit 8 whose input 9 is electrically coupled via a switch 10 either to the output of the current pulse shaper 5 for changing the shape of current pulses (position I of the switch 10), to produce the second level of the first stage of general electroanesthesia, or to the output of the intermittent analgesia unit 3 (position II of the switch 10), to counteract growing pain.

The device also includes a unit 11 for adjusting the value of an additional constant component. The input 12 of the additional constant component value adjusting unit 11 is connected to an output 13 of the power source 7, which permits the reduction of the impedance at the points where there are applied electrodes, i.e., a split cathode 14 and a split anode 15 (shown conventionally). The electrodes are of the conventional type. The cathode 14 is attached in the forehead area, whereas the anode 15 is attached in the neck area, under the mastoids, in order to produce the second level of the first stage of general electroanesthesia in the central nervous system of the patient.

Inputs 16 and 17, 18 and 19 of the current pulse preamplification unit 8 and the unit 11 for adjusting the value of the additional constant component, respectively, are connected to the output 6 of the power unit 7 and to outputs 20 and 21 of a patient protection unit 22. This limits the level of general electroanesthesia, while acting with current pulses on the central nervous system, in accordance with an anesthesia and treatment program prescribed for each patient. Outputs 23 and 24 are connected to inputs 25 and 26 of a unit 27 for adjusting the amplitude of current pulses.

An input 28 of the patient protection unit 22 and an input 29 of the unit 27 for adjusting the amplitude of current pulses are connected to the output 6 of the power unit 7.

Outputs 30, 31 and 32 of the unit 27 for adjusting the amplitude of current pulses are respectively connected to inputs 33 and 34 of the patient protection unit 22, a current pulse amplitude indicator 35 and a mean current intensity indicator 36 to whose output the cathode 14 and the anode 15 are connected.

FIG. 2 is a circuit diagram of the units 3, 4, 5, 7, 8, 11, 22, 27 and 35.

The units 1, 2 and 36 are of the conventional type.

The intermittent analgesia unit 3 (FIG. 3) for intermittent analgesia in the course of child delivery is a counting flip-flop built around transistors 37 and 38, resistors 39, 40, 41 and 42, capacitors 43 and 44, and diodes 45 and 46.

At the point of connection of the diodes 45 and 46, one input of the intermittent analgesia unit 3 is coupled to the output of the unit 2 for separate adjustment of the repetition frequency and duration of current pulse. The other input of the unit 3 is connected to the output 6 of the power source 7.

The output of the intermittent analgesia unit 3 is the electrode of the transistor 38 and is connected to the input of the unit 4 for adjusting the duration of current pulses and to the switch 10.

The unit 4 for adjusting the duration of current pulses is a one-shot multivibrator with collector-base capacitive couplings, built around transistors 47 and 48, resistors 49, 50, 51, 52 and 53, a variable resistor 54 and capacitors 55, 56 and 57. The variable resistor 54 serves to adjust the duration of current pulses acting on the central nervous system.

One input of the unit 4 for adjusting the duration of current pulses is the capacitor 57 and is connected to the output of the intermittent analgesia unit. The other input of the unit 4 is connected to the output 6 of the power unit 7.

The unit 5 for changing the shape of current pulses comprises a pulse shaper or former which produces pulses with an exponential fall of the trailing edge. The unit 5 is built around a common-collector transistor 58, resistors 59 and 60, and capacitors 61 and 62.

The selection of the pulse shape of the output signal is determined by the position of a switch 63. The switch 63 serves as one of the inputs of the unit 5 for changing the shape of current pulses and is connected to the output of the unit 4 for adjusting the duration of current pulses, i.e., to the collector electrode of the transistor 48. The other input of the unit 5 is connected to the output 6 of the power unit 7.

The output of the unit 4, i.e., the collector electrode of the transistor 48, is connected to the base electrode of the transistor 58 or to the switch 10 in accordance with the position of the switch 63 of the current pulse shaper unit 5.

The output of the unit 5 for changing the shape of current pulses, i.e., the switch 63, is connected to the switch 10. When in position II, the switch 10 provides for intermittent analgesia from contraction to contraction at a constant on-off time ratio equal to two. When in position I, the switch 10 permits the production of the second level of the first stage of general electroanesthesia at a variable on-off time ratio.

The current pulse preamplification unit 8 is built around a common-emitter transistor 64 and a resistor 65. The transistor 64 serves for amplitude preamplification of current pulses acting on the central nervous system.

The input 9 of the current pulse preamplification unit 8 is the base electrode of the transistor 64 and is connected to the switch 10. The input 18 of the unit 8 is connected to the output 6 of the power unit 7. The input 18 of the unit 8, i.e., the emitter electrode of the transistor 64, is connected to the output 20 of the patient protection unit 22. The output 23 of the current pulse preamplification unit 8 is the collector electrode of the transistor 64 and is connected to the input 25 of the unit 27 for adjusting the amplitude of current pulses.

The patient protection unit 22 is built around common-collector transistors 66 and 67, a variable resistor 68 and a capacitor 69. The combined base electrodes of the transistors 66 and 67 are connected to the variable resistor 68. This permits the limitation of the level of general electroanesthesia in accordance with an anesthesia and treatment program prescribed for each patient.

The output 20 of the patient protection unit 22, i.e., the emitter electrode of the transistor 66, is connected to the input 18, i.e., the emitter electrode of the transistor 64 of the current pulse preamplification unit 8. This permits the setting of a current pulse amplitude in accordance with an anesthesia and treatment program prescribed for each patient. The output 21 of the patient protection unit 22, i.e., the emitter electrode of the transistor 67, is connected to the input 19 of the unit 11 for adjusting the value of the additional constant component. The input 28 of the unit 22 is connected to the output 6 of the power unit 7. The output 30 of the current pulse amplitude adjusting unit 27 is connected to the input 33 of the patient protection unit 22 at the point of connection of the variable resistor 68 and the capacitor 69.

The unit 11 for adjusting the value of the additional constant component is built around a common-emitter transistor 70, a resistor 71 and a variable resistor 72 which makes it possible to adjust the level of the additional constant component.

The input 12 of the unit 11 for adjusting the value of the additional constant component, i.e., the variable resistor 72, is connected to the output 13 of the power unit 7 which incorporates a means for feeding the additional constant component. The input 17 of the unit 11 is connected to the output 6 of the power unit 7. The input 19 of the unit 11, i.e., the emitter electrode of the transistor 70, is connected to the output 21 of the patient protection unit 22, i.e., the emitter electrode of the transistor 67. The output 24 of the unit 11 for adjusting the value of the additional constant component, i.e., the collector electrode of the transistor 70, is connected to the input 26 of the unit 27 for adjusting the amplitude of current pulses.

The unit 27 for adjusting the amplitude of current pulses is a voltage generator built around transistors 73 and 74, which ensure a constant output voltage, irrespective of changes in the impedance at the points where the electrodes are attached in the forehead and neck areas, resistors 75, 76, 77 and 78, a variable resistor 79 and a capacitor 80, which permits the maintenance of the second level of the first stage of general electroanesthesia, irrespective of changes in the functional state of the patient's central nervous system.

The input 25 of the unit 27 for adjusting the amplitude of current pulses acting on the central nervous system, i.e. the variable resistor 79, is connected to the output 23 of the current pulse preamplification unit 8. The output 24, or the collector electrode of the transistor 70 of the additional constant component value adjusting unit 11, is connected to the input 26 of the current pulse amplitude adjusting unit 27 at the point of connection of the resistor 75, the variable resistor 79 and the capacitor 80. The of the unit 27, i.e., the resistor 76, is connected to the input 33 of the patient protection unit 22 at the point of connection of the variable resistor 68 and the capacitor 69. This makes it possible to carry out an anesthesia and treatment program prescribed for each patient. The output 31 of the unit 27 is connected to the input 34 of the current pulse amplitude indicator 35. The output 32 of the unit 27, i.e., the emitter electrode of the transistor 74, is connected to the mean current intensity indicator 36.

The current pulse amplitude indicator 35 is a peak detector built around a transistor 81, a capacitor 82, and a diode 83. The unit 35 also includes a measuring instrument 84. The input 34 of the unit 35 is connected to the output 31 of the unit 27 for adjusting the amplitude of current pulses.

The power unit 7 comprises a voltage converter, a rectifier, a voltage source and a means for supplying the additional constant component. The voltage converter is built around transistors 85 and 86, resistors 87, 88, 89 and 90, and a transformer 91. The voltage converter also includes a switch 92 electrically connected to a voltage source 93. The rectifier is built around a resistor 94, a capacitor 95 and a diode 96. The means for supplying the additional constant component is connected via the output 13 to the input 12 of the unit 11 for adjusting the value of the additional constant component; the function of this means is performed by the resistor 90.

The operating principle of the device of the invention for pulse current action on the central nervous system is as follows.

The cathode 14 (FIG. 1) is attached to the patient's forehead, and the anode 15 is attached in the neck area, under the mastoids, in order to produce the second level of the first stage of general electroanesthesia in the central nervous system of the patient.

In order to produce the second level of the first stage of general electroanesthesia, the unit 1 for rhythmic current pulse action on the central nervous system produces a train of square pulses of a predetermined frequency (a pulse signal) which is applied to the intermittent analgesia unit 3 via the unit 2 for separate adjustment of the repetition frequency and duration of current pulses. The intermittent analgesia unit 3 forms a train of square pulses with a constant on-off time ratio equal to two, which is used to counteract growing pain through the intermittent analgesia technique.

The same train of pulses is applied to the unit 4 for adjusting the duration of current pulses which permits the production of the second level of the first stage of general electroanesthesia without any side effects on the patient. A signal of desired direction is supplied from the output of the unit 4, to the unit 5 for changing the shape of the current pulses. Pulses with an exponential decline of the trailing edge are used to anesthetize weak patients and children.

The signal is supplied to the input 9 of the current pulse preamplification unit 8 via the switch 10 in its position I. The signal is supplied from the output 23 of the current pulse preamplification unit 8 to the input of the unit 27.

The variable resistor 79 (FIG. 2) of the unit 27 for adjusting the amplitude of current pulses permits the adjustment of the amplitude of current pulses acting on the central nervous system of the patient. This ensures a constant second level of the first stage of general electroanesthesia, regardless of changes in the functional state of the patient's central nervous system.

The measuring instrument 84 of the current pulse amplitude indicator measures the amplitude of the current. The measuring instrument 84, in combination with the mean current intensity indicator 36 (FIG. 1), makes it possible to check the depth of anesthesia upon reaching the second level of the first stage of general electroanesthesia.

The train of pulses is supplied to the circuit of the cathode 14 attached to the patient's forehead and to the circuit of the anode 15 attached in the neck area, under the mastoids, via the mean current intensity indicator 36.

In order to reduce the impedance at the points where the electrodes are attached, the application of the pulse signal formed at the output 32 of the unit 27 for adjusting the amplitude of current pulses is accompanied by applying the additional constant component to the electrodes. This serves to speed up the attainment of the second level of the first stage of general electroanesthesia. The additional constant component is applied to the electrodes from the output 13 of the power unit 7 via the input 12 of the unit 11 for adjusting the value of the additional contant component, the output 24 of the unit 11, the input 26 of the unit 27, the output 32 of the unit 27 and the unit 36.

As the switch 10 is set in position II, a pulse signal with a constant on-off time ratio equal to two is provided at the output 32 of the unit 27 for adjusting the amplitude of current pulses. This pulse signal is supplied to the electrodes, i.e., the cathode 14 and the anode 15 via the main current intensity indicator 36. This makes it possible to counteract the worst surges of pain.

The patient protection unit 22 has no effect upon the operation of the current pulse preamplification unit 8 and the unit 11 for adjusting the value of the additional constant component when the mean current intensity in the patient circuit is not in excess of a prescribed level set in the unit 22 via the variable resistor 68 (FIG. 2). In this case, the second level of the first stage of general electroanesthesia is produced in the known manner.

When the mean current intensity rises above the prescribed level, the patient protection unit 22 (FIG. 1) reduces the amplitude of the pulse signal at the output 23 of the unit 8 and reduces the value of the additional constant component at the output 24 of the unit 11.

Thus, the output signal at the points where the electrodes are attached can never be in excess of a prescribed level, irrespective of the changes in the impedance. This feature of the device of the invention ensures complete protection of the patient in case of an increase in the mean current intensity caused by a reduction in the impedance at the points where the electrodes are attached, and makes it unnecessary to discontinue operation of the device.

At the same time, the constant pulse action level maintained by the device of the invention eliminates the need for a medical staff to continuously check the current pulse action and attend to a patient throughout a period of application of current pulse anesthesia and treatment.

What is claimed is:

1. A device for pulse current action on the central nervous system, comprising
   a rhythmic current pulse action unit for rhythmic current pulse action on the central nervous system of a patient, having an input and an output;
   an intermittent analgesia unit having an output, a first input and a second input electrically connected to said output of said rhythmic current pulse action unit;
   a current pulse duration adjusting unit for adjusting the duration of current pulses acting on the central nervous system for producing the second level of the first stage of general electroanesthesia in the central nervous system of the patient without any side effects on said patient, having an output, a first input electrically connected to said output of said intermittent analgesia unit, and a second input;
   a switch selectively electrically connected to said output of said current pulse duration adjusting unit and to said output of said intermittent analgesia unit;
   a current pulse preamplification unit having an output, a first input selectively electrically connected via said switch to said output of said current pulse duration adjusting to produce the second level of the first stage of general electroanesthesia, and to said output of said intermittent analgesia unit to counteract growing pain, a second input and a third input;
   a current pulse amplitude adjusting unit for adjusting the amplitude of current pulses acting on the central nervous system of the patient, having a first output, a second output, a third output, a first input connected to said output of said current pulse preamplification unit, a second input and a third input;
   a mean current intensity indicator having an output and an input connected to said first output of said current pulse amplitude adjusting unit;
   an anode connected to said output of said mean current intensity indicator and attachable to the neck area of the patient, under the mastoids;
   a cathode connected to said output of said mean current intensity indicator and attachable to the forehead area of the patient,
   said anode and said cathode permitting the production of the second level of the first stage of general electroanesthesia in the central nervous system of said patient;
   an additional constant component value adjusting unit having a first input, a second input, a third input and an output connected to said second input of said current pulse amplitude adjusting unit;
   a power unit having a first output connected to said first input of said additional constant component value adjusting unit for permitting the reduction of the impedance at the points where said anode and cathode are attached to the neck and forehead areas, respectively, and a second output;
   a patient protection unit having a first output, a second output, a first input connected to said second output of said current pulse amplitude adjusting unit, and a second input, said current pulse preamplification unit and said additional constant component value adjusting unit being connected at their respective second inputs to said second output of said power unit, and at their respective third inputs to said first and second outputs of said patient protection unit to limit the level of general electroanesthesia, while acting with pulse currents on the central nervous system of the patient, according to an anesthesia and treatment program prescribed for each patient, said second output of said power unit being connected to said input of said rhythmic current pulse action unit, to said second input of each of said intermittent analgesia unit, said current pulse duration adjusting unit and said patient protection unit, and to said third input of said current pulse amplitude adjusting unit; and a current pulse amplitude indicator having an input connected to said third output of said current pulse amplitude adjusting unit.

2. A device for pulse current action on the central nervous system, comprising a rhythmic current pulse action unit for rhythmic current pulse action on the central nervous system of a patient, having an input and an output;

an intermittent analgesia unit having an output, a first input and a second input electrically connected to said output of said rhythmic current pulse action unit;

a current pulse duration adjusting unit for producing the second level of the first stage of general electroanesthesia in the central nervous system of said patient without any side effects on said patient, having an output, a first input electrically connected to said output of said intermittent analgesia unit, and a second input;

a current pulse shaping unit for changing the shape of current pulses for producing the second level of the first stage of general electroanesthesia in weak patients and children, having an output, a first input connected to said output of said current pulse duration adjusting unit, and a second input;

a switch selectively electrically connected to said output of said current pulse shaping unit and to said output of said intermittent analgesia unit;

a current pulse preamplification unit having an output, a first input selectively electrically connected via said switch and said current pulse shaping unit to said output of said current pulse duration adjusting unit to produce the second level of the first stage of general electroanesthesia, and via said switch alone to said output of said intermittent analgesia unit to counteract growing pain;

a current pulse amplitude adjusting unit having a first output, a second output, a third output, a first input connected to said output of said current pulse preamplification unit, a second input and a third input;

a mean current intensity indicator having an output and an input connected to said first output of said current pulse amplitude adjusting unit;

an anode connected to said output of said mean current intensity indicator and attachable to the neck area, under the mastoids;

a cathode connected to said output of said mean current intensity indicator and attachable to the forehead area of the patient, said anode and cathode permitting the production of the second level of the first stage of general electroanesthesia in the central nervous system of said patient;

an additional constant component value adjusting unit having a first input, a second input, a third input and an output connected to said second input of said current pulse amplitude adjusting unit;

a power unit having a first output connected to said first input of said additional constant component value adjusting unit for permitting the reduction of the impedance at the points where the anode and cathode are attached to the forehead and neck areas, and a second output;

a patient protection unit having a first output, a second output first input connected to said second output of said current pulse amplitude adjusting unit, and a second input, said current pulse preamplification unit and said additional constant component value adjusting unit being connected at their respective second inputs to said second output of said power unit, and at their third inputs to said first and second outputs of said patient protection unit to limit the level of general electroanesthesia, while acting with pulse currents on the central nervous system of the patient, in accordance with an anesthesia and treatment program prescribed for each patient, said second output of said power unit being connected to said input of said rhythmic current pulse action unit, to said second input of each of said intermittent analgesia unit, said current pulse duration adjusting unit, said current pulse shaping unit and said patient protection unit, and to said third input of said current pulse amplitude adjusting unit; and a current pulse amplitude indicator having an input connected to said third output of said current pulse amplitude adjusting unit.

3. A device for pulse current action on the central nervous system, comprising a rhythmic current pulse action unit for rhythmic current pulse action on the central nervous system of a patient, having an input and an output;

a current pulse repetition frequency and duration adjustment unit for separate adjustment of the repetition frequency and duration of current pulses for ensuring a specific approach to each patient upon producing the second level of the first stage of general electroanesthesia, having an output, a first input connected to said output of said rhythmic current pulse action unit, and a second input;

an intermittent analgesia unit having an output, a first input and a second input electrically connected to said output of said current pulse repetition frequency and duration adjustment unit;

a current pulse duration adjusting unit for producing the second level of the first stage of general electroanesthesia in the central nervous system of the patient without any side effect on said patient, having an output, a first input electrically connected to said output of said intermittent analgesia unit, and a second input;

a current pulse shaping unit for changing the shape of current pulses for producing the second level of the first stage of general electroanesthesia in weak patients and children, having an output, a first input connected to said output of said current pulse duration adjusting unit, and a second input;

a switch selectively electrically connected to said output of said current pulse shaping unit and to said output of said intermittent analgesia unit;

a current pulse preamplification unit having an output, a first input selectively electrically connected via said switch and said current pulse shaping unit to said output of said current pulse duration adjusting unit to produce the second level of the first stage of general electroanesthesia, and via said switch alone to said output of said intermittent analgesia unit to counteract growing pain;

a current pulse amplitude adjusting unit having a first output, a second output, a third output, a first input connected to said output of said current pulse preamplification unit, a second input and a third input;

a mean current intensity indicator having an output and an input connected to said first output of said current pulse amplitude adjusting unit;

an anode connected to said output of said mean current intensity indicator and attachable to the neck area of the patient, under the mastoids;

a cathode connected to said output of said mean current intensity indicator and attachable to the forehead area of the patient, said anode and cathode permitting the production of the second level of the first stage of general electroanesthesia in the central nervous system of said patient;

an additional constant component value adjusting unit having a first input, a second input, a third input and an output connected to said second input of said current pulse amplitude adjusting unit;

a power unit having a first output connected to said first input of said additional constant component value adjusting unit for permitting the reduction of the impedance at the points where said anode and cathode are attached in the neck and forehead areas, respectively, and a second output;

a patient protection unit having a first output, a second output, a first input connected to said second output of said current pulse amplitude adjusting unit, and a second input, said current pulse preamplification unit and said additional constant component value adjusting unit being connected at their respective second inputs to the second output of said power unit, and at their respective third inputs to said first and second outputs of said patient protection unit to limit the level of general electroanesthesia, while acting with pulse currents on the central nervous system of the patient, in accordance with an anesthesia and treatment program prescribed for each patient, said second output of said power unit being connected to said input of said rhythmic current pulse action unit, to said second input of each of said current pulse repetition frequency and duration adjustment unit, said intermittent analgesia unit, said current pulse duration adjusting unit, said current pulse shaping unit and said patient protection unit, and to said third input of said current pulse amplitude adjusting unit; and a current pulse amplitude indicator having an input connected to said third output of said current pulse amplitude adjusting unit.

4. A device for pulse current action on the central nervous system, comprising a rhythmic current pulse action unit for rhythmic current pulse action on the central nervous system of a patient, having an input and an output;

a current pulse repetition frequency and duration adjustment unit for separate adjustment of the repetition frequency and duration of current pulses for ensuring a specific approach to each patient upon producing the second level of the first stage of general electroanesthesia, having an output, a first input connected to said output of said rhythmic current pulse action unit, and a second input;

an intermittent analgesia unit having an output, a first input and a second input electrically connected to said output of said current pulse repetition frequency and duration adjustment unit;

a current pulse duration adjusting unit for producing the second level of the first stage of general electroanesthesia in the central nervous system of the patient without any side effects on said patient, having an output, a first input electrically connected to said output of said intermittent analgesia unit, and a second input;

a current pulse shaping unit for changing the shape of current pulses for producing the second level of the first stage of general electroanesthesia in weak patients and children, having an output, a first input connected to said output of said current pulse duration adjusting unit, and a second input;

a switch selectively electrically connected to said output of said current pulse shaping unit and to said output of said intermittent analgesia unit;

a current pulse preamplification unit having an output, a first input selectively electrically connected via said switch and said current pulse shaping unit to said output of said current pulse duration adjusting unit to produce the second level of the first stage of general electroanesthesia, and via said switch alone to said output of said intermittent analgesia unit to permit the counteracting of growing pain;

a current pulse amplitude adjusting unit having a first output, a second output, a third output, a first input connected to said output of said current pulse preamplification unit, a second input and a third input, said current pulse amplitude adjusting unit comprising a voltage generator thereby permitting the maintenance of the second level of the first stage of general electroanesthesia regardless of changes in the functional state of the central nervous system of said patient;

a mean current intensity indicator having an output and an input connected to said first output of said current pulse amplitude adjusting unit;

an anode connected to said output of said mean current intensity indicator and attachable to the neck area of the patient under the mastoids;

a cathode connected to said output of said mean current intensity indicator and attachable to the forehead area of the patient, said anode and cathode permitting the production of the second level of the first stage of general electroanesthesia in the central nervous system of said patient;

an additional constant component value adjusting unit having a first input, a second input, a third input and an output connected to said second input of said current pulse amplitude adjusting unit;

a power unit having a first output connected to said first input of said additional constant component value adjusting unit for permitting the reduction of the impedance at the points where said anode and cathode are attached in the neck and forehead areas, respectively, and a second output;

a patient protection unit having a first output, a second output, a first input connected to said second output of said current pulse amplitude adjusting unit, and a second input, said current pulse preamplification unit and said additional constant component value adjusting unit being connected at their respective second inputs to said second output of said power unit, and at their respective third inputs to said first and second outputs of said patient protection unit to permit limitation of the level of general electroanesthesia, while acting with pulse currents on the central nervous system of the patient, in accordance with an anesthesia and treatment program prescribed for each patient, said second output of said power unit being connected to said input of said rhythmic current pulse action unit, to said second input of each of said current pulse repetition frequency and duration adjustment unit, said intermittent analgesia unit, said current pulse duration adjusting unit, said current pulse shaping unit and said patient protection unit, and to said third input of said current pulse amplitude adjusting unit; and a current pulse amplitude indicator having an input connected to said third output of said current pulse amplitude adjusting unit.

* * * * *